United States Patent [19]

Littleford, deceased et al.

[11] Patent Number: 5,179,961

[45] Date of Patent: Jan. 19, 1993

[54] CATHETER GUIDING AND POSITIONING METHOD

[76] Inventors: Philip O. Littleford, deceased, late of Winter Park, Fla.; by H. Richard Bates, personal representative, 322 E. Central Blvd., Orlando, Fla. 32801

[21] Appl. No.: 769,969

[22] Filed: Oct. 2, 1991

Related U.S. Application Data

[62] Division of Ser. No. 337,475, Apr. 13, 1989, Pat. No. 5,054,500.

[51] Int. Cl.⁵ .............................................. A61B 5/00
[52] U.S. Cl. ..................................... 128/772; 604/96; 604/101
[58] Field of Search ....................... 128/657, 772, 784; 604/96, 101, 103, 158, 164, 171, 280

[56] References Cited

U.S. PATENT DOCUMENTS

| | | | |
|---|---|---|---|
| 3,882,852 | 5/1975 | Sinnreich | 604/96 |
| 3,884,242 | 5/1975 | Bazell et al. | 604/103 |
| 3,913,565 | 10/1975 | Kawahara | 128/772 |
| 4,040,413 | 8/1977 | Ohshiro | 604/101 |
| 4,100,246 | 7/1978 | Frisch | 604/101 |
| 4,141,364 | 2/1979 | Schultze | 604/96 |
| 4,166,469 | 9/1979 | Littleford | 128/784 |
| 4,265,848 | 5/1981 | Rusch | 604/96 |
| 4,545,390 | 10/1985 | Leary | 128/772 |
| 4,763,654 | 8/1988 | Jang | 604/101 |
| 4,782,834 | 11/1988 | Maguire et al. | 604/96 |

FOREIGN PATENT DOCUMENTS 8901755 3/1989 World Int. Prop. O. ............. 604/96

Primary Examiner—Max Hindenburg
Attorney, Agent, or Firm—Allen, Dyer, Doppelt, Franjola & Milbrath

[57] ABSTRACT

An apparatus and method for guiding and centering a catheter to a treatment site within a passageway in the human body includes a flexible tube having a distal end dimension to pass freely along the passageway, and a proximal end adapted to extend outside the body. The flexible tube is provided with a peripherally expandable zone at the distal end of the tube and a longitudinal lumen through the flexible tube dimension for passing a catheter therethrough. The distal end of the flexible tube is guided to a desired location within the passageway. The peripheral zone at the distal end of the tube is then expanded so that the expandable zone pushes against the inner wall of the passageway to center the distal end of the tube within the passageway. With the tube positioned within the passageway, a catheter is passed through the longitudinal lumen of the flexible tube.

6 Claims, 2 Drawing Sheets

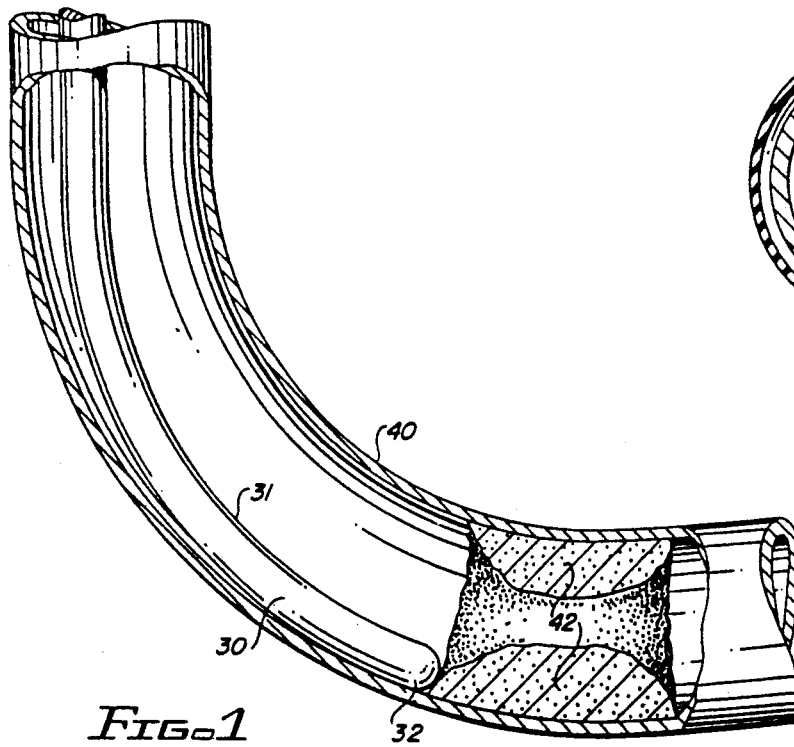
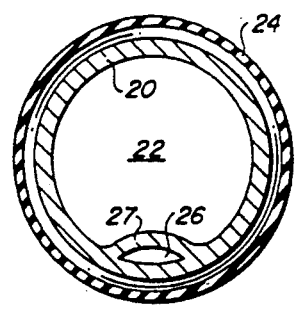
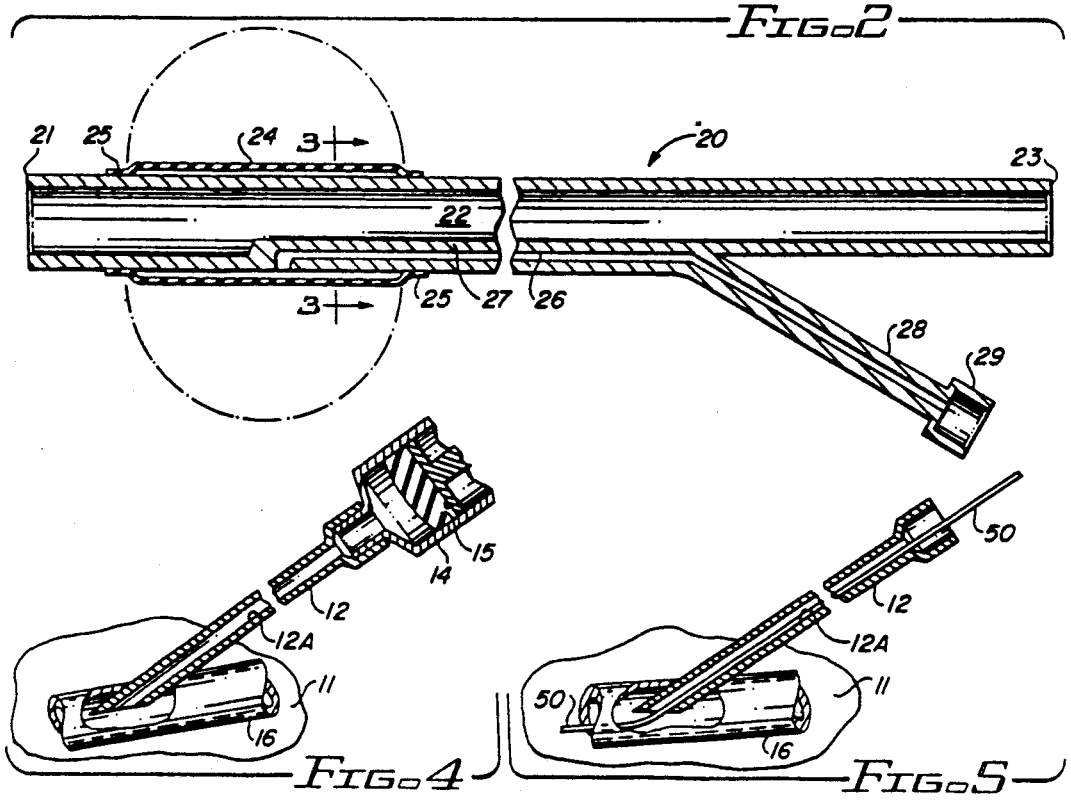
Fig. 1 (PRIOR ART)
Fig. 2
Fig. 3
Fig. 4
Fig. 5

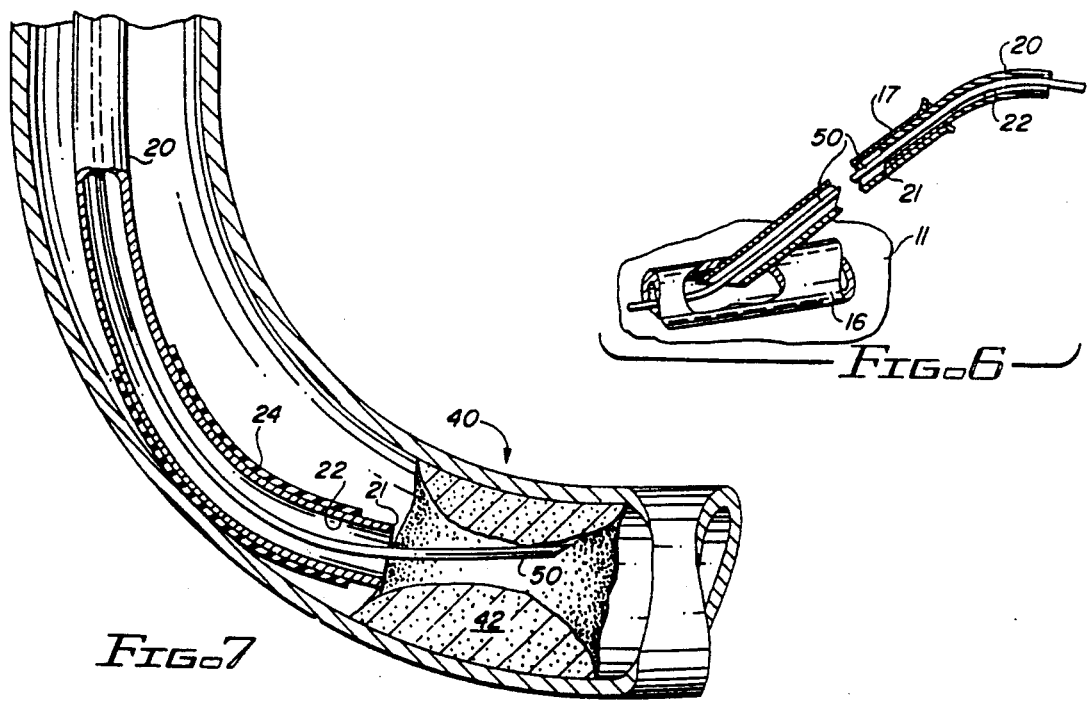
FIG. 6
FIG. 7
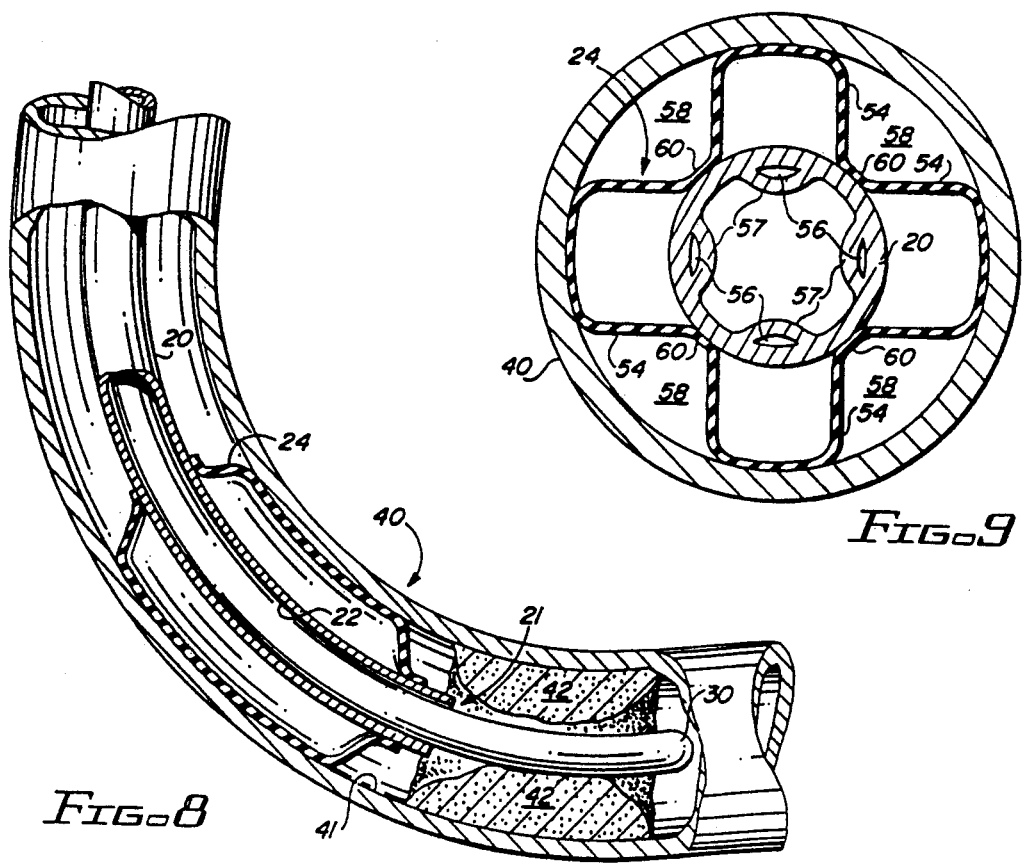
FIG. 8
FIG. 9

CATHETER GUIDING AND POSITIONING METHOD

This is a divisional of co-pending application Ser. No. 07/337,475 filed Apr. 13, 1989, U.S. Pat. No. 5,054,500.

BACKGROUND OF THE INVENTION

1. Field of the Invention

This invention relates to apparatus and methods for guiding and positioning medical catheters.

2. Description of the Prior Art

A catheter is a medical device which is introduced into a body channel or blood vessel for a variety of purposes. For example, one type is known as an intra-aortic balloon catheter which is used for cardiac assistance. Such catheters are frequently introduced into the body through the femoral artery because of the large diameter and accessibility of that artery. After insertion into the femoral artery, the distal end of the catheter must be pushed through the appropriate blood vessels to the location to be treated, e.g. an occluded blood vessel near the heart. The catheter also has a proximal end extending outside the body by which the distal end is manipulated and maneuvered. Since the path along which the catheter passes is frequently tortuous, then the task of guiding and positioning the catheter is often difficult.

It is also sometimes necessary to remove the first catheter and insert a second catheter in its place. Further, once the distal end of the catheter reaches its desired location, it is often improperly positioned or extending angularly in the wrong direction, thus precluding the effective use of the catheter.

Prior art pertaining to apparatus and method for positioning catheters within tubular passageways in the human body include the following U.S. Pat. Nos. 4,456,011 to Warnecke; 4,445,892 to Hussein, et al.; 4,423,725 to Baran, et al.; 4,418,688 to Loeb; 4,411,654 to Boarini, et al.; 4,409,971 to LeVeen, et al.; 4,349,029 to Mott; 4,346,698 to Hanson et al.; 4,335,723 to Patel; 4,327,709 to Hanson et al; 4,261,339 to Hanson et al.; 4,114,618 to Vargas; 3,952,742 to Taylor; 3,837,347 to Tower; 3,394,705 to Abramson; and 2,687,131 to Raiche.

SUMMARY OF THE INVENTION

Among the several objects of the present invention is the provision of an improved apparatus and method for guiding and positioning a catheter. The apparatus and method of the present invention provides for the guiding of the catheter to a desired location within a blood vessel in a human body by way of a catheter guiding apparatus having an elongated guiding tube with a longitudinal lumen dimensioned to receive the catheter. By properly positioning the elongated tube through the blood vessel, the catheter can be properly positioned in the tube to communicate with the blood vessel. The guiding catheter also includes means for centering the distal end of the catheter within the blood vessel for effective use. In a preferred embodiment, this means comprises an inflatable membrane on the distal end of the elongated tube with means for inflating the membrane once the distal end of the tube is at the desired location within the blood vessel, thereby achieving the centering of the distal end.

In general, the method and apparatus of the present invention contemplate a guiding catheter in the form of a flexible tube having a distal end to be inserted into the body and a proximal end adapted to extend outside the body. The flexible tube is dimensioned to pass freely along the passageway and has a longitudinal lumen dimensioned to receive a treatment catheter which is to be properly positioned at a treatment site within the patient's body. The guiding catheter has an inflatable positioning balloon at the distal end of the tube and an auxillary lumen for controlling inflation of the positioning balloon. In use, the guiding catheter is positioned at the treatment site, and the positioning balloon is extended against the wall of the tubular passageway to center the distal end of the guiding catheter within the passageway. Thereafter, the treatment catheter is then passed through the longitudinal lumen to conduct the desired treatment at the site.

DESCRIPTION OF THE DRAWING

FIG. 1 is a side view, partly in section, of a conventional catheter within a blood vessel;

FIG. 2 is a side view, in cross-section of the catheter guiding apparatus of the present invention;

FIG. 3 is a cross-sectional view taken along the line 3—3 in FIG. 2;

FIGS. 4, 5 and 6 are perspective views, partly in cross-section, illustrating the steps of inserting the guiding catheter apparatus into a blood vessel;

FIG. 7 is a side view in cross-section of the guiding catheter within a blood vessel;

FIG. 8 is a side view, in cross-section, like that of FIG. 7, with the expandable balloon inflated to center the guiding catheter within the blood vessel.

FIG. 9 is a cross-sectional view of another embodiment of the guiding catheter in which the inflatable balloon permits fluids, such as blood, to pass over the inflatable balloon.

Corresponding reference characters indicate corresponding parts throughout the several views of the drawings.

The exemplifications set out herein illustrate the preferred embodiments of the present invention in one form thereof, and such exemplifications are not to be construed as limiting either the scope of the invention or the scope of the disclosure thereof in any manner.

DETAILED DESCRIPTION OF THE PREFERRED EMBODIMENT

Reference is made to FIG. 1 which illustrates a conventional treatment catheter 30 within a blood vessel 40. The blood vessel 40 is shown having an occlusion 42 through which it is desired to insert the treatment catheter 30 in order to, for example, remove the occlusion 42 with laser energy or open the occlusion with an angioplasty balloon. The treatment catheter 30 has a distal end 32 adapted for insertion into a human body and a proximal end (not shown) extending outside the human body. By way of example, the catheter 30 may be inserted through the femoral artery in the groin of a patient, pushed through the aorta and directed to the occlusion 42, which may be located in the region of the patient's heart.

The distal end 32 is directed through the blood vessel 40 by twisting and manipulating the proximal end of the catheter 30 Generally a fluoroscope is used to view the distal end 32 so that its position and orientation is known. Since positioning of the distal end 32 is controlled via the proximal end, directing the distal end 32 through the blood vessel 40 is often difficult if the blood vessel 40 is tortuous. Even if the distal end 32 of the catheter 30 is longitudinally positioned within the blood vessel 40, it may not be oriented radially with respect to the blood vessel 40. For example, the distal end 32 may press against the inner wall of the blood vessel 40, as shown in FIG. 1, rather than being centered within the blood vessel 40.

FIGS. 2-8 illustrate one form of the apparatus and method for guiding and positioning the catheter 30 along the blood vessel 40 at the desired treatment site. The guiding catheter, referred to generally by reference numeral 20, has a distal end 21 dimensioned to pass freely along the blood vessel 40 and a proximal end 23 adapted to extend outside the human body. The guiding catheter 20 has a longitudinal lumen 22 dimensioned for receiving the treatment catheter 30. The guiding catheter 20 is further provided with a radially expandable balloon 24 at the distal end 21 of the tube 20 and which balloon is preferably formed integrally as a portion of the side wall of the guiding catheter 20. In the practice of this method of guiding a catheter, such as catheter 30 in FIG. 1, the distal end 21 of the tube 20 is guided to a desired location at the treatment site, such as blood vessel 40, and the balloon 24 is radially expanded such that the balloon 24 pushes against the wall 41 of the blood vessel 40 to center the distal end 21 of the tube 20.

The guiding catheter 20 may be formed of any suitable material having the necessary flexibility characteristics, such as for instance inert, non-toxic elastomeric materials. Flexibility of the tube 20 is required so that the tube 20 can pass through the tortuous paths of typical blood vessels, particularly in the cardiovascular area.

The distal end 21 of the guiding catheter 20 is provided with an expandable balloon 24 in the form of a sleeve radially disposed about the tube 20. The balloon 24 may be formed of any suitable material such as for instance an elastomeric polymer and is sufficiently thin that it is freely expanded with little force. The edges 25 of the balloon 24 are bonded to the tube 20 by way of an appropriate adhesive, or by heat sealing the edges 25 to the distal end 21.

An inflation lumen 26 is provided within the guiding catheter 20 and in communication with the balloon 24 to transport fluid to the balloon 24. The inflation lumen 26 is defined between the inside diameter of the tube 20 and an inner panel 27 formed, preferably, of the same material and thickness as the guiding catheter 20. An inflation tube 28, adapted to extend outside the human body during use, communicates with the inflation lumen 26. The inflation tube 28 is provided with a proximal end 29 adapted to receive the needle of a syringe (not shown) whereby the balloon 24 is inflated, denoted by phantom membrane 24a, by injecting under pressure a fluid such as for instance a glucose or saline solution. Preferably, the wall of the balloon 24 is much thinner that the wall of the guiding catheter 20 and inner panel 24 so that the guiding catheter 20 and inner panel 24 do not deform substantially when subject to the fluid pressure required to inflate the balloon 24.

FIGS. 4-8, inclusive, illustrate the manner of insertion and use of the present invention.

FIGS. 4-6 show the use of an introducer, as taught in U.S. Pat. No. 4,166,469, to introduce the guiding catheter 20 into a blood vessel, such as the femoral artery 16. In this procedure, a needle 12 is provided for puncturing the exterial skin 11 of the patient to enter the femoral artery 16. A piston 15 of a syringe 14 is withdrawn slightly to draw a small quantity of blood from the femoral artery 16 to ensure that the needle 12 has entered the femoral artery 16. The syringe 14 is then removed from the needle 12. A flexible guidewire 50, having a diameter sufficiently small to enter through the internal passage 12A of the needle 12, is pushed through the needle 12 to enter the femoral artery 16 as shown in FIG. 5. The needle 12 is then removed, enabling the distal end 21 of the guiding catheter 20 is passed over the guidewire 50 and into the femoral artery 16. The flexible tube 20 and the guidewire 50 located in the longitudinal lumen 22 are directed to the desired treatment site within the blood vessel 40, such as for instance an occlusion 42 as shown in FIG. 7. The guidewire 50 adds some rigidity to the tube 20 to help urge the tube 20 through the blood vessel 40.

As shown in FIG. 8, after the distal end 21 of the guiding catheter 20 id placed adjacent the treatment site, then the balloon 24 is expanded by injecting a fluid into the inflation lumen 26. As the wall of the balloon 24 expands, the balloon wall presses-against the inner walls of the blood vessel 40 to constrain the flexible tube 20 within the blood vessel 40 as well as to center the flexible tube 20. With the flexible tube 20 in place, the guide wire 50 is removed and a catheter 30 is inserted through the longitudinal lumen 22 so that the distal end 32 of the catheter 30 communicates with the occlusion 42. Preferably, the distal end 21 of the tube 20 is positioned such that the distal end 32 of the catheter 30 is oriented in the direction of the longitudinal axis of the blood vessel 40 rather than, for instance, in a direction toward the wall of the blood vessel 40. Orienting the catheter 30 in the axial direction is accomplished by making the membrane 24 sufficiently long and sufficiently elastic such that a substantial longitudinal portion of the membrane 24 contacts the blood vessel 40. By having a substantial portion of the membrane 24 contacting the blood vessel 40, the force which the membrane 24 exerts on the tube 20 is distributed along the portion of the tube 20 positioned radially inward of the membrane 24 to radially center that portion within the blood vessel 40. If a small longitudinal portion of the membrane 24 contacts the wall of the blood vessel 40, the distal end 21 of the tube 20 may be positioned to direct the catheter 30 toward the wall of the blood vessel 40 rather than the longitudinal axis, even though the distal end 21 of the tube is centered within the blood vessel 40. Additionally, having a substantial portion of the membrane 24 contacting the blood vessel 40 minimizes the fluid pressure required to position the tube 20 within the blood vessel 40 and, consequently, minimizes possible tissue damage.

FIG. 9 illustrates a cross-sectional view of another embodiment of the expandable membrane 24 of FIGS. 2 and 3 which permits blood flow through the blood vessel 40 while the tube 20 is positioned within the blood vessel 40. In this embodiment, four longitudinal portions 60 of the membrane 24 are secured to the outer diameter of the tube 20 by way of an appropriate adhesive or by heat sealing to effectively create four longitudinal balloons 54. Four inflation lumens 56 are provided within the tube 20, each communicating with a corresponding one of the longitudinal balloons 54 to transport fluid to the balloons 54, thus effectuating inflation thereof. Each inflation lumen 56 is defined between the inside diameter of the tube 20 and an inner panel 57 formed, preferably, of the same material and thickness as the tube 20 with the edges of the inner panel 57 being secured to the tube 20 by way of an appropriate adhesive or by heat sealing. As fluid is injected, under pressure, through the lumen 56 to communicate with the balloons 54, the balloons 54 inflate and push against the interior of the blood vessel 40 to center the flexible tube 20 within the blood vessel 40. With the balloons 54 fully expanded within the blood vessel 40, fluid channels 58 are defined between the balloons 54. Creation of the fluid channels 58 prevents the expanded membrane 24 from completely blocking the blood vessel 40 and thereby restricting blood flow through the blood vessel 40. In this manner, the flexible tube 20 may remain in the blood vessel 40 for longer periods of time.

While the principles of the invention have now been made clear in an illustrative embodiment, it will become obvious to those skilled in the art, many modifications in structure, arrangement, portions and components used in the practice of the invention and otherwise which are particularly adapted for specific operating requirements without departing from those principles. Accordingly, it is intended that the description be interpreted as illustrative and not in a limiting sense.

What is claimed is:

1. A method for aligning a treatment catheter used in treating an arterial blockage in an artery of a patient comprising the steps of:

providing a guiding catheter having a distal end dimensioned for extension into the artery of the patient, the guiding catheter having a longitudinal lumen extending through the guiding catheter and through its distal extremity, the guiding catheter further comprising means for aligning the distal end within the artery and means for operating the aligning means;

extending the distal end of the guiding catheter into the artery and adjacent to, and short of the arterial blockage;

operating the aligning means to align the distal extremity of the longitudinal lumen with the arterial blockage;

guiding the treatment catheter through the longitudinal lumen and its distal extremity and then to the arterial blockage; and thereafter treating the arterial blockage with the treatment catheter.

2. The method recited in claim 1 further comprising the step of maintaining blood flow through the artery during the step of operating the aligning means.

3. The method recited in claim 1 wherein the aligning means comprises the inflatable membrane about the periphery of the distal end, and wherein the step of operating the aligning means comprises the step of inflating the peripheral member outwardly against the inner periphery of the artery.

4. The method recited in claim 1 wherein the artery under treatment is a heart artery, and wherein the step of extending the distal end of the guiding catheter into the artery comprises the step of cannulating the femoral artery of the patient.

5. The method recited in claim 1 further comprising the steps of:

extending a guidewire through the artery to the arterial blockage;

extending the guiding catheter along the guidewire; and then removing the guidewire while leaving the guiding catheter in place.

6. The method recited in claim 1 wherein the treatment catheter comprises an angioplasty balloon catheter, and wherein the treating step further comprises extending the angioplasty balloon catheter through the arterial blockage.

* * * * *